(12) United States Patent
Spivey et al.

(10) Patent No.: US 10,596,559 B2
(45) Date of Patent: Mar. 24, 2020

(54) ACIDIC CATALYST

(71) Applicants: James J. Spivey, Baton Rouge, LA (US); Kunlun Ding, Baton Rouge, LA (US); Swarom Kanitkar, Baton Rouge, LA (US)

(72) Inventors: James J. Spivey, Baton Rouge, LA (US); Kunlun Ding, Baton Rouge, LA (US); Swarom Kanitkar, Baton Rouge, LA (US)

(73) Assignee: Board of Supervisors of Louisana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 16/403,172

(22) Filed: May 3, 2019

(65) Prior Publication Data

US 2019/0262813 A1 Aug. 29, 2019

Related U.S. Application Data

(63) Continuation of application No. 15/867,920, filed on Jan. 11, 2018, now Pat. No. 10,328,422.

(Continued)

(51) Int. Cl.
| | |
|---|---|
| *B01J 27/10* | (2006.01) |
| *B01J 29/70* | (2006.01) |
| *B01J 27/06* | (2006.01) |
| *B01J 29/40* | (2006.01) |
| *B01J 37/02* | (2006.01) |

(Continued)

(52) U.S. Cl.
CPC ............ *B01J 29/70* (2013.01); *B01J 27/06* (2013.01); *B01J 29/041* (2013.01); *B01J 29/40* (2013.01); *B01J 37/0209* (2013.01); *C07C 2/76* (2013.01); *C07C 5/2705* (2013.01); *C07C 5/2708* (2013.01); *C07C 2521/04* (2013.01); *C07C 2521/08* (2013.01); *C07C 2527/08* (2013.01);

(Continued)

(58) Field of Classification Search
CPC . B01J 29/40; B01J 29/041; B01J 29/70; B01J 27/06; B01J 27/10
USPC .......................................... 502/63, 224, 231
See application file for complete search history.

(56) References Cited

U.S. PATENT DOCUMENTS

| | | |
|---|---|---|
| 2,519,034 A | 8/1950 | Elmore |
| 2,678,957 A | 5/1954 | Fontana |

(Continued)

FOREIGN PATENT DOCUMENTS

CN 10 4447846 3/2015

OTHER PUBLICATIONS

Vasireddy, Sivakumar Direct conversion of methane to higher hydrocarbons using AlBr3—HBr superacid catalyst, ChemComm, Nov. 17, 2010, http://pubs.rsc.org.

(Continued)

*Primary Examiner* — Patricia L. Hailey
(74) *Attorney, Agent, or Firm* — John B. Edel; Edel Patents LLC

(57) ABSTRACT

Catalysts are disclosed having metal oxide support structures and acidic reaction sites. Those reaction sites may have multiple bromine atoms bound to an aluminum atom with that aluminum-bromine group having an associated hydrogen ion. Additional structural features of the reaction sites are dictated by the aluminum oxide based catalysts and a silicon oxide based catalyst selected.

4 Claims, 2 Drawing Sheets

Related U.S. Application Data

(60) Provisional application No. 62/488,466, filed on Apr. 21, 2017.

(51) Int. Cl.
  *C07C 2/76* (2006.01)
  *C07C 5/27* (2006.01)
  *B01J 29/04* (2006.01)

(52) U.S. Cl.
  CPC .. *C07C 2527/125* (2013.01); *C07C 2527/126* (2013.01); *C07C 2529/70* (2013.01)

(56) References Cited

U.S. PATENT DOCUMENTS

| | | |
|---|---|---|
| 3,182,013 A | 5/1965 | Myers |
| 3,914,383 A | 10/1975 | Kirsch et al. |
| 5,294,578 A | 3/1994 | Ho |
| 5,451,704 A | 9/1995 | Ho |
| 2002/0183465 A1 | 12/2002 | Babcock |
| 2018/0304241 A1* | 10/2018 | Spivey .................. B01J 29/041 |

OTHER PUBLICATIONS

Dissertation by Wu, "Acidity and Catalytic Activity of Zeolite Catalysts Bound With Silica and Alumina", Texas A&M University, Dec. 2003, Abstract. (Year: 2003).

* cited by examiner

ACIDIC CATALYST

This application is a continuation of prior application Ser. No. 15/867,920 filed Jan. 11, 2018 and entitled Acidic Catalyst which claims the benefit of U.S. Provisional Application No. 62/488,466 filed on Apr. 21, 2017 and entitled Acidic Catalyst.

his invention was made with government support under grant award number CBET-1644895 awarded by the National Science Foundation. The government has certain rights in the invention.

Acidic catalyst described herein may be used in hydrocarbon reactions. Certain acidic catalyst disclosed herein demonstrate super acidity and may be capable of isomerizing alkanes at room temperature. Certain acidic catalyst disclosed herein may be useful in the oligomerization of methane.

DETAILED DESCRIPTION

Example Set 1A

Initial Catalyst

Figure 1:
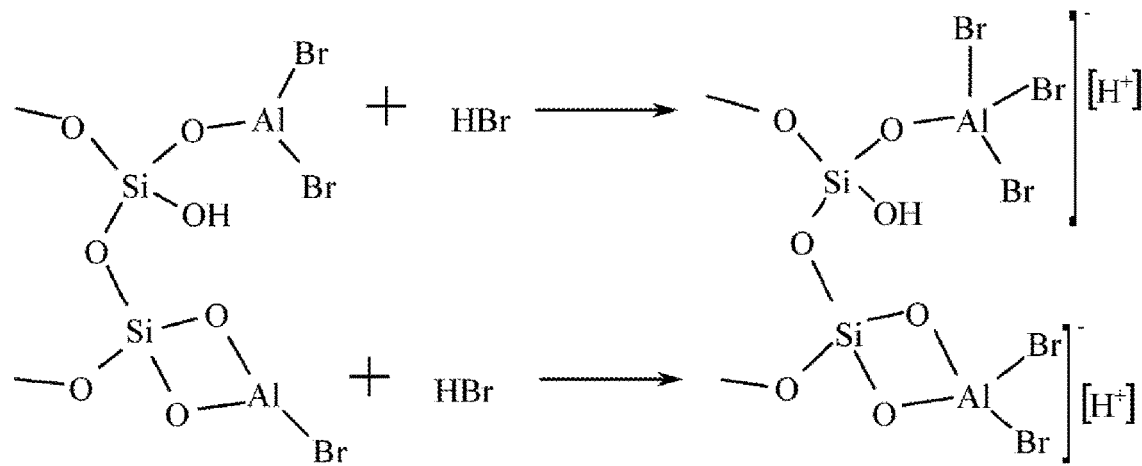
FIG. 1 shows an acidification reaction.

Wet impregnation techniques may be used with various solvents to prepare acid catalysts. For example, supports may be impregnated by the dissolved aluminum halide precursors represented by the aluminum species of Table 1 in solvents of Table 1 at room temperature with reflux producing the initial catalyst species shown in Table 1. The resulting catalysts may then be filtered and dried under vacuum yielding solid acid catalysts represented by initial catalyst species Ai-Pi.

TABLE 1

| Initial | Support | Solvent | Al Species | Augmented Acid Catalyst |
| --- | --- | --- | --- | --- |
| $A_i$ | Alumina | Toluene | $AlCl_3$ | $A_a$ |
| $B_i$ | Alumina | $CCl_4$ | $AlCl_3$ | $B_a$ |
| $C_i$ | Alumina | Toluene | $AlBr_3$ | $C_a$ |
| $D_i$ | Alumina | $CHBr_3$ | $AlBr_3$ | $D_a$ |
| $E_i$ | Silica Gel | Toluene | $AlCl_3$ | $E_a$ |
| $F_i$ | Silica Gel | $CCl_4$ | $AlCl_3$ | $F_a$ |
| $G_i$ | Silica Gel | Toluene | $AlBr_3$ | $G_a$ |
| $H_i$ | Silica Gel | $CHBr_3$ | $AlBr_3$ | $H_a$ |
| $I_i$ | MCM-41 | Toluene | $AlCl_3$ | $I_a$ |
| $J_i$ | MCM-41 | $CCl_4$ | $AlCl_3$ | $J_a$ |
| $K_i$ | MCM-41 | Toluene | $AlBr_3$ | $K_a$ |
| $L_i$ | MCM-41 | $CHBr_3$ | $AlBr_3$ | $L_a$ |
| $M_i$ | SBA-15 | Toluene | $AlCl_3$ | $M_a$ |
| $N_i$ | SBA-15 | $CCl_4$ | $AlCl_3$ | $N_a$ |
| $O_i$ | SBA-15 | Toluene | $AlBr_3$ | $O_a$ |
| $P_i$ | SBA-15 | $CHBr_3$ | $AlBr_3$ | $P_a$ |

Example Set 1B

Initial Catalyst

Vapor phase grafting techniques may also be used to prepare acid catalysts. For example, supports and aluminum halide, separated by quartz wool, may be heated up to 300° C. inside an air free vessel or under an inert atmosphere, allowing aluminum halide vapor to react with the surface species of support producing the initial catalyst species shown in Table 1. The resulting catalysts may then be separated from aluminum halide under vacuum yielding solid acid catalysts represented by initial catalyst species $A_i$-$P_i$. In one example, not shown in Table 1, $AlBr_3$ was grafted onto ZSM-5 according to the method described above to produce an $AlBr_3$ modified ZSM-5 initial catalyst.

The supports used are not limited to the supports described in Table 1. Other supports consistent with the present disclosure may include zeolites and other similar supports. Such supports may be microporous supports or mesoporous supports. Supports may be silica-based or they may be alumina based. Inorganic supports may be used particularly when elevated temperatures are contemplated for later uses of resulting catalyst.

Example Set 2

Acidification

Initial catalyst species $A_i$-$P_i$ may then be treated with HBr to form acid sites analogous to $[H^+/AlBr_4^-]$ and $[H^+/AlCl_3Br^-]$. Examples of HBr treatment that may be used to further acidify initial catalyst species $A_i$-$P_i$ include contacting initial catalyst species $A_i$-$P_i$ with a flow of between 1% and 10% HBr gas in an inert gas such as helium or argon for a duration between one and three hours at room temperature. HBr concentrations may more broadly range between 0.1% and 20% HBr. Each of the HBr treatments occur at room temperature but may be performed at higher temperatures potentially enhancing the acidity of the catalyst. For example, the HBr treatment may occur between 50° C. and 200° C. The product of the HBr treatment of initial catalyst species $A_i$-$P_i$ is the augmented acid catalyst $A_a$-$P_a$. As an example, the silica gel based initial catalyst species $G_i$ may react with HBr to yield $G_a$ as follows:

That acidification of the initial catalyst to yield the augmented acid catalyst may be generally characterized by the reaction depicted in FIG. 1 with that figure showing the reaction sites of augmented acid catalyst $G_a$. Other augmented acid catalyst would vary from augmented acid catalyst $G_a$ based on the choice of support and aluminum species. Augmented acid catalyst $G_a$, $K_a$, $O_a$ and $C_a$ have been produced and verified in the laboratory according to the described methods and augmented acid catalyst $A_a$, $B_a$, $D_a$, $E_a$, $F_a$, $H_a$, $I_a$, $J_a$, $L_a$ $M_a$, $N_a$ and $P_a$ along with other similar alumina and silica based catalysts are prophetic embodiments that may be produced according the methods described herein.

Figure 2:
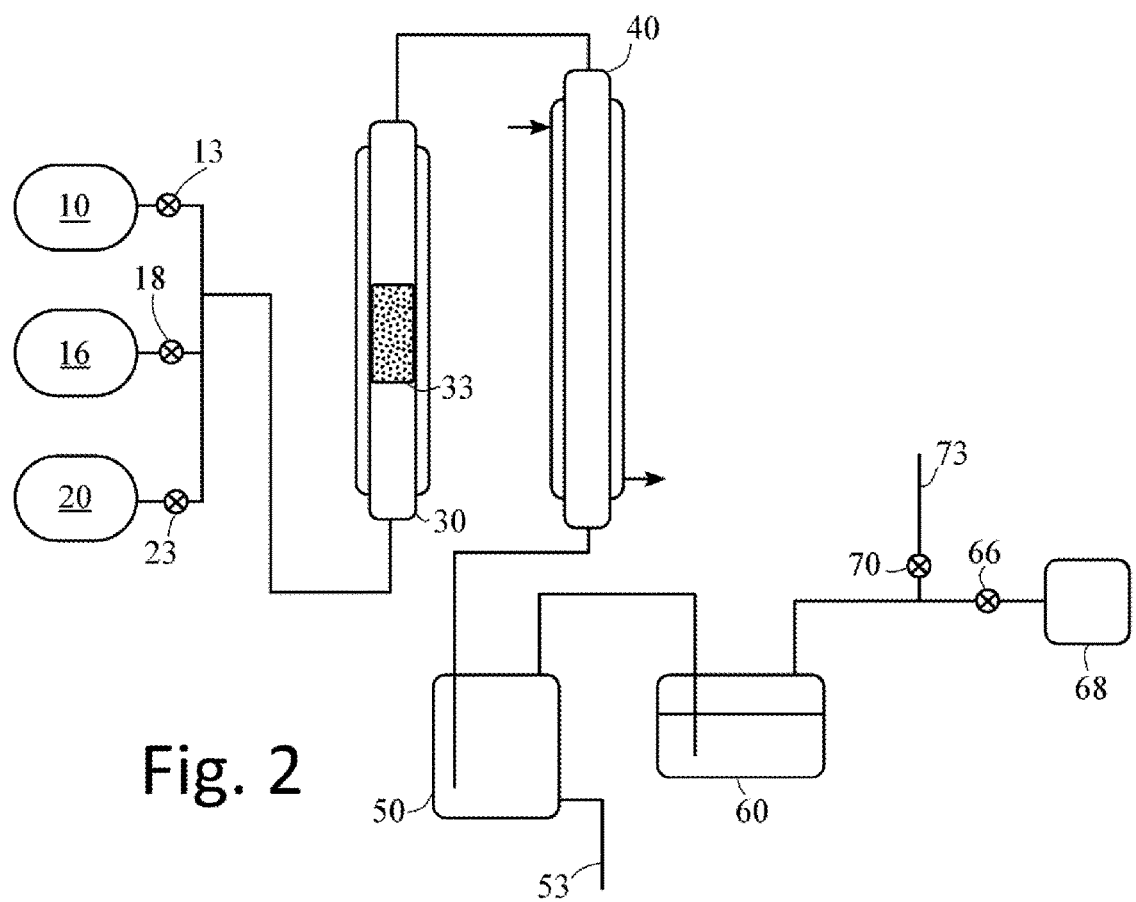
FIG. 2 shows a reactor setup.

The reactor set up of FIG. 2 may be used for the acidification reactions of the present example set and in methane oligomerization. FIG. 2 depicts Methane supply 10, Methane supply valve 13, HBr supply 16, HBr supply valve 18, Helium supply 20, Helium supply valve 23, Tubular reactor 30, Catalyst bed 33, Condenser 40, Gas-liquid separation unit 50, Liquid drain 53, Caustic wash vessel 60, Gas chromatograph valve 66, Gas chromatograph 68, Vent valve 70 and Vent 73. HBr acidification may occur by passing HBr and helium over Catalyst bed 33 in Tubular reactor 30 such that the acidification of example set two is achieved. Caustic wash vessel 60, which may contain a KOH solution, removes unreacted HBr from the effluent gas. Methane oligomerization may also be conducted in the reactor setup as described herein.

Example Set 3

Forms

Augmented acid catalysts may take the form of catalysts having reaction sites according to one or more of the following general formulas:

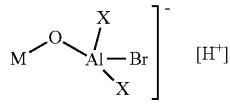
(1)

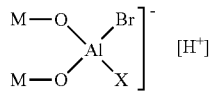
(2)

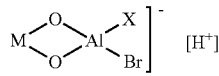
(3)

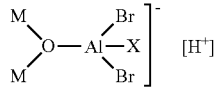
(4)

In general formulas 1-4, X may be Br or Cl and M may be either Si or Al. Further, M would be molecularly bound to a support structure such as those described herein. General formula 5 is a generalization of various forms of the described reaction sites.

$$[M_xO_yAlBr_zX]^-H^+ \tag{5}$$

In general formula 5, x is selected from 1 and 2; y is selected from 1 and 2; z is selected from 1 and 2; X is selected from Br and Cl; and M is selected from Al and Si. Further, in general formula 5, one or more of M, O and Al would have a molecular bond with the metal oxide support structure.

Augmented acid catalysts with metal oxide support structures may take the form of catalysts having acidic reaction sites according to one or more of the following general formulas:

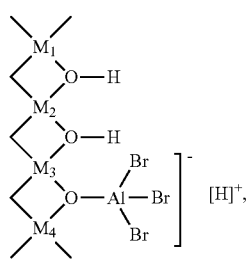
(6)

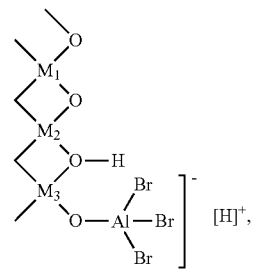
(7)

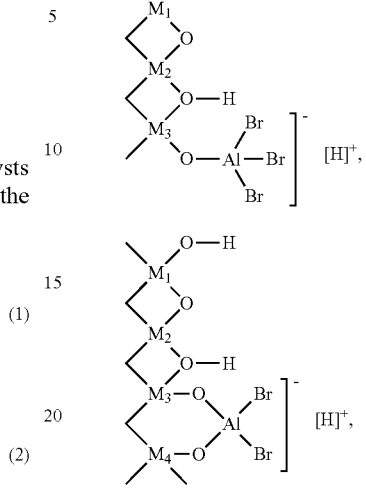
(8)

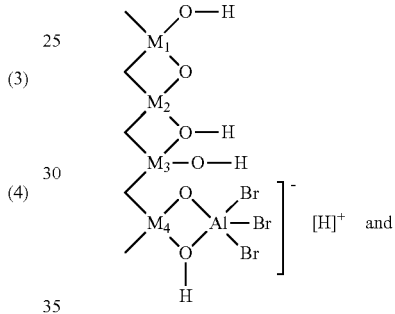
(9)

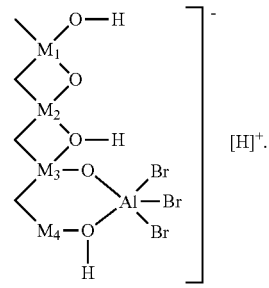
(10)

In the above general formulas 6-10, $M_1$, $M_2$, $M_3$ and $M_4$, when present, are selected from a first group in which $M_1$ is Al, $M_2$ is Al, $M_3$ is Al and $M_4$ is Al and a second group in which $M_1$ is Si, $M_2$ is selected from Si and Al, $M_3$ is Si and $M_4$ is Si. In those examples, the catalyst is selected from an aluminum oxide based catalyst and a silicon oxide based catalyst. Also, the $AlCl_3$ may be the aluminum halide species used to create the augmented acid catalyst. Also, the open-ended bonds depicted in the general formulas connect the acidic reaction site to the metal oxide support structure. One or more of the compositions of general formulas 6-10 may be produced by the wet impregnation techniques of Example Set 1A combined with the Acidification of Example Set 2. One or more of the compositions of general formulas 6-10 are produced by the vapor phase grafting Example Set 1B combined with the Acidification of Example Set 2.

In a subset of the examples associated with general formulas 6-10, $M_1$ may be Al, $M_2$ may be Al, $M_3$ may be Al and $M_4$, when present, may be Al. Such examples may be present when Alumina is the substrate.

In a subset of the examples associated with general formulas 6-10, $M_1$ may be Si, $M_2$ may be Al, $M_3$ may be Si and $M_4$, when present, may be Si. Such examples may be present when one of MCM-41, SBA-15 or ZSM-5 is the substrate.

In a subset of the examples associated with general formulas 6-10, $M_1$ may be Si, $M_2$ may be Si, $M_3$ may be Si and $M_4$, when present, may be Si. Such examples may be present when one of MCM-41, SBA-15 or silica gel is the substrate.

Example Set 4

Isomerization

Certain augmented acid catalyst may be characterized as superacids based on the ability of those catalyst to isomerize n-butane into isobutane. As that term is used herein "superacid" designates compounds and catalysts capable of n-butane isomerization at room temperature. Such testing may be conducted in a continuous flow reactor in which n-butane flows over a bed of the subject catalyst at room temperature. In such testing, the augmented acid catalyst $G_a$, $K_a$ and $O_a$ demonstrated super acidity and $C_a$ did not demonstrate super acidity.

Example Set 5A

Oligomerization Tests

Augmented acid catalyst $A_a$-$P_a$ along with other similar catalysts may be subjected to methane oligomerization methods or test such as presented in FIG. 2. FIG. 2 depicts the general reaction setup of the present example set. The conversion of methane may be evaluated with a gas chromatograph and other standard equipment for the evaluation of hydrocarbon products. Higher molecular weight hydrocarbons may be captured from Gas-liquid separation unit 50 and Caustic wash vessel 60 for analysis. The contacting of the methane with the catalyst may occur at a variety of temperatures and pressures including room temperature and atmospheric pressure. Further elevated temperatures, elevated pressures or both may be used. For example, elevated temperatures and pressures commonly associated with conventional hydrocarbon processing may be used. Each of initial catalyst species $A_i$-$P_i$ and each of augmented acid catalyst $A_a$-$P_a$ have significant potential utility as acid catalysts or as superacid catalyst regardless of those compounds ability to oligomerize methane.

Augmented acid catalyst $C_a$, $G_a$, $K_a$ and $O_a$, each prepared using the wet impregnation technique, have been tested for methane oligomerization and did not demonstrate measured methane oligomerization in preliminary tests. Augmented acid catalyst $A_a$, $B_a$, $D_a$, $E_a$, $F_a$, $H_a$, $I_a$, $J_a$, $L_a$, $M_a$, $N_a$ and $P_a$ are each individually significant candidates for successful methane oligomerization and the prophetic methods of contacting the methane with the augmented acid catalyst $A_a$, $B_a$, $D_a$, $E_a$, $F_a$, $H_a$, $I_a$, $J_a$, $L_a$, $M_a$, $N_a$ and $P_a$ are directly intended as methods of the present disclosure. Oligomerization may have been masked by trace organic compounds in reaction tests using catalyst prepared with wet impregnation techniques and for that reason, augmented acid catalyst $C_a$, $G_a$, $K_a$ and $O_a$ may still be candidates for oligomerization. Methane oligomerization, as described herein may be generally characterized as the conversion of methane to higher molecular weight hydrocarbons and may proceed according to the following generalized reaction in which n is greater than or equal to 2:

$$n\text{CH}_4 \rightarrow C_nH_m + x\text{H}_2$$

Example 5B

Oligomerization

Methane gas was co-fed with HBr into Tubular reactor 30, as described in FIG. 1, such that the combined gas flowed over the $AlBr_3$ modified ZSM-5 initial catalyst described in Example Set 1B. An analysis of the product gas indicated that oligomerization had occurred resulting in multiple higher molecular weight hydrocarbon species. Further analysis of products ruled out the HBr acting as a reactant.

Example Set 5C

Oligomerization

Figure 3:
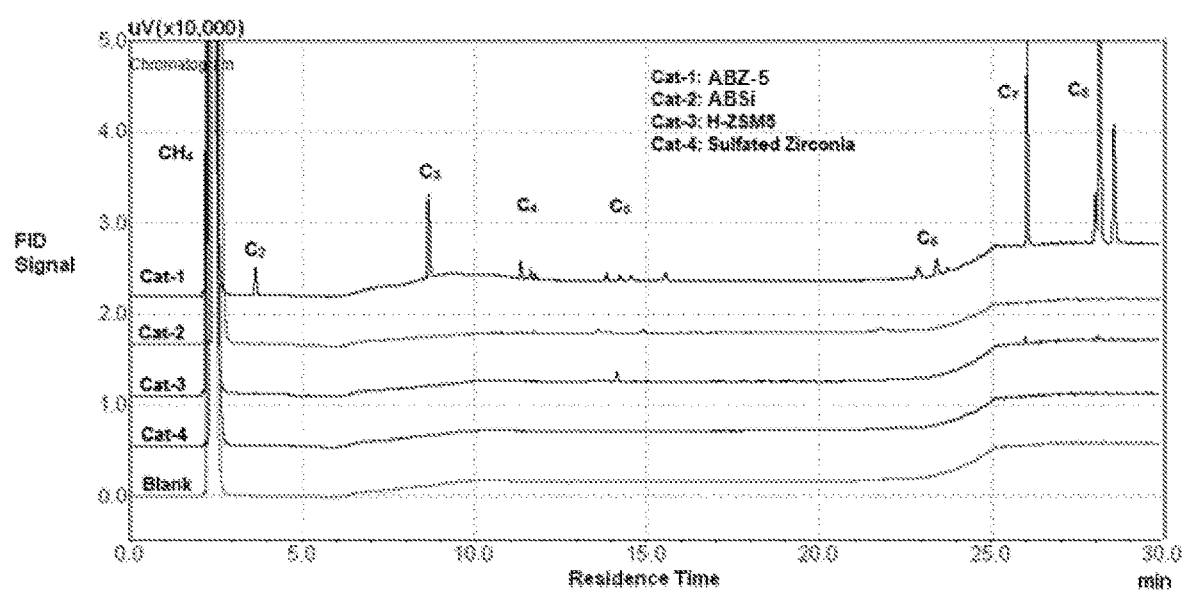
FIG. 3 shows chromatogram results for attempted oligomerization reactions.

In four separate attempted oligomerization reactions, using the reaction setup of FIG. 1, methane gas was fed without HBr into a reactor such that the methane gas flowed over four catalysts. $CH_4$ was oligomerized over the $AlBr_3$ supported on H-ZSM5, noted as "ABZ-5" and "Cat-1;" $AlBr_3$ supported on $SiO_2$, noted as "ABSi" and "Cat-2;" unmodified H-ZSM5 noted as "Cat-3" and over sulfated zirconia, noted as "Cat-4." Of the four separate attempted oligomerization reactions of the present example set, only $AlBr_3$ supported on H-ZSM5 produced a range of hydrocarbons, from $C_2$-$C_8$, including ethylene, propylene, butenes, butane, pentenes, as well as aromatics including benzene, toluene and xylenes. The other catalysts showed no measurable products. Each of these four attempted oligomerization reactions were conducted at approximately 300° C., 1 atm, 9 L/gcat-hr. FIG. 3 shows a chromatograph that compares the four $CH_4$ attempted oligomerization runs.

Accordingly, oligomerization may occur using an initial catalyst with or without the co-feeding of HBr and oligomerization may occur using an augmented catalyst with or without the co-feeding of HBr.

As that phrase is used herein, a "mesoporous catalyst" is a catalyst having an average pore diameter between 2 and 50 nm. As that phrase is used herein, a "microporous catalyst" is a catalyst having an average pore diameter that is at most 2 nm. As that phrase is used herein, an "aluminum oxide based catalyst" is a metal oxide catalyst in which aluminum is the elemental metal having the greatest individual weight percent among all elemental metals present in the metal oxide catalyst. Alumina, for example would be an aluminum oxide based catalyst. As that phrase is used herein, a "silicon oxide based catalyst" is a metal oxide catalyst in which silicon is the elemental metal having the greatest individual weight percent among all elemental metals present in the metal oxide catalyst. Silica Gel, MCM-41 and SBA-15 would each be considered silicon oxide based catalyst as that phrase is used herein. The phrases aluminum oxide based catalyst and silicon oxide based catalyst as used herein are intended to encompass augmented acid catalyst $A_a$-$P_a$. Silica-alumina mixed oxide catalysts may be characterized as either aluminum oxide based catalyst or silicon oxide based catalyst as those phrases are used herein based on the weight of elemental metals present in the silica-alumina mixed oxide catalyst. For example, a zeolite according to the formula $Na_2Al_2Si_3O_{10} \cdot 2H_2O$ would be a silicon oxide based catalyst. As used herein Si is treated as a metal for the purposes of describing metal oxide catalyst, silicon oxide based catalyst, aluminum oxide based catalyst and the like.

Compositions of matter described herein may, for example, comprise a catalyst comprising a metal oxide support structure and an acidic reaction site such that the acidic reaction site has a composition according to a general formula,

in which x is 1 or 2; y is 1 or 2; z is 1 or 2; X is Br or Cl; M is Al or Si; one or more of M, O and Al has a molecular bond with the metal oxide support structure and the catalyst is an aluminum oxide based catalyst or a silicon oxide based catalyst. In a related example, the catalyst may be a mesoporous catalyst. In a related example, the catalyst may be a microporous catalyst. In a related example, the catalyst may be an aluminum oxide based catalyst. In a further related example, the catalyst may be a silicon oxide based catalyst. In a further related example, X may be Br. In a further related example, X may be Cl. In a further related example, M may be Al. In a still further related example, M may be Si. In a still further related example, M may be Si and X may be Br. In a still further related example, M may be Si and X may be Cl.

Compositions of matter described herein may, for example, comprise a catalyst comprising a metal oxide support structure and an acidic reaction site such that the acidic reaction site has a composition according to a general formula,

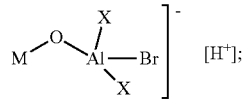

in which X is Br or Cl; M is Al or Si; one or more of M and O has a molecular bond with the metal oxide support structure and the catalyst is an aluminum oxide based catalyst or a silicon oxide based catalyst. In a related example, the catalyst may be a mesoporous catalyst. In a related example, the catalyst may be a microporous catalyst. In a related example, the catalyst may be an aluminum oxide based catalyst. In a further related example, the catalyst may be a silicon oxide based catalyst. In a further related example, X may be Br. In a further related example, X may be Cl. In a further related example, M may be Al. In a still further related example, M may be Si. In a still further related example, M may be Si and X may be Br. In a still further related example, M may be Si and X may be Cl.

Compositions of matter described herein may, for example, comprise a catalyst comprising a metal oxide support structure and an acidic reaction site such that the acidic reaction site has a composition according to a general formula,

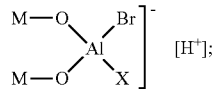

in which X is Br or Cl; M is Al or Si; one or more of M and O has a molecular bond with the metal oxide support structure and the catalyst is an aluminum oxide based catalyst or a silicon oxide based catalyst. In a related example, the catalyst may be a mesoporous catalyst. In a related example, the catalyst may be a microporous catalyst. In a related example, the catalyst may be an aluminum oxide based catalyst. In a further related example, the catalyst may be a silicon oxide based catalyst. In a further related example, X may be Br. In a further related example, X may be Cl. In a further related example, M may be Al. In a still further related example, M may be Si. In a still further related example, M may be Si and X may be Br. In a still further related example, M may be Si and X may be Cl.

Compositions of matter described herein may, for example, comprise a catalyst comprising a metal oxide support structure and an acidic reaction site such that the acidic reaction site has a composition selected from the general formulas:

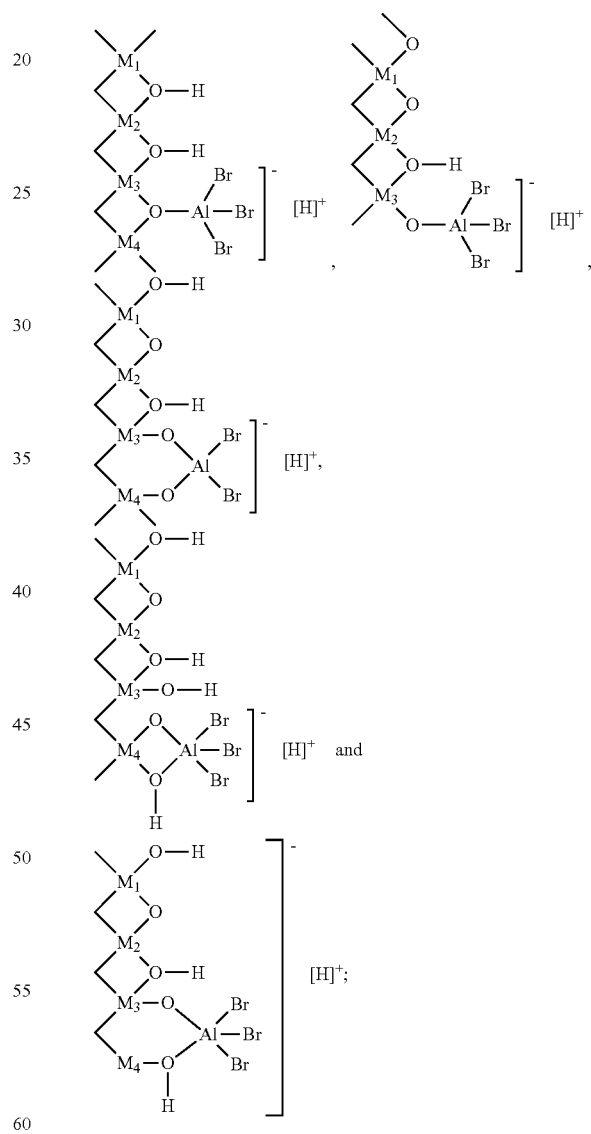

$M_1$, $M_2$, $M_3$ and $M_4$, when present, may be selected from: a first group in which $M_1$ is Al, $M_2$ is Al, $M_3$ is Al and $M_4$ is Al, a second group in which $M_1$ is Si, $M_2$ is Si, $M_3$ is Si and $M_4$ is Si and a third group in which $M_1$ is Si, $M_2$ is Al, $M_3$ is Si and $M_4$ is Si; the catalyst may be selected from an aluminum oxide based catalyst and a silicon oxide based catalyst and such that the open-ended bonds depicted in the general formulas connect the acidic reaction site to the metal oxide support structure.

As that phrase is used herein, a "light hydrocarbon composition," is a composition comprising a one to four carbon atom hydrocarbon. Thus, natural gas would be an example of a light hydrocarbon composition.

Methods of reacting hydrocarbons described herein may comprise providing a light hydrocarbon composition having a first constituent molecule and a second constituent molecule; providing a catalyst; bringing the catalyst in contact with the light hydrocarbon composition and conducting a chemical reaction in which the first constituent molecule reacts with the second constituent molecule to produce a product molecule having a higher molecular weight than the first constituent molecule; such that the catalyst is selected from an aluminum oxide based catalyst and a silicon oxide based catalyst and such that the catalyst is an acidic catalyst. In a related example, the catalyst may be a mesoporous catalyst. In a related example, the catalyst may be a microporous catalyst. In a related example, the catalyst may be an aluminum oxide based catalyst. In a related example, the catalyst may be a silicon oxide based catalyst. In a related example, the conducting of the chemical reaction may be done in the presence of HBr. In a related example, the first constituent molecule is methane and the second constituent molecule is methane.

The above-described embodiments have a number of independently useful individual features that have particular utility when used in combination with one another including combinations of features from embodiments described separately. There are, of course, other alternate embodiments which are obvious from the foregoing descriptions, which are intended to be included within the scope of the present application.

What is claimed is:

1. A composition of matter comprising:
   a. a catalyst comprising a metal oxide support structure and an acidic reaction site;
   b. wherein the acidic reaction site has a composition selected from the general formulas:

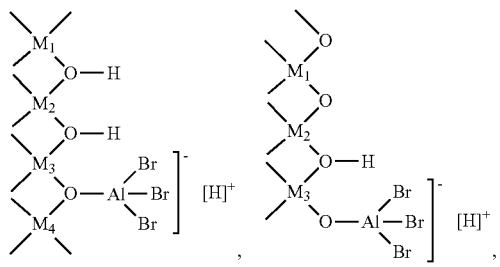

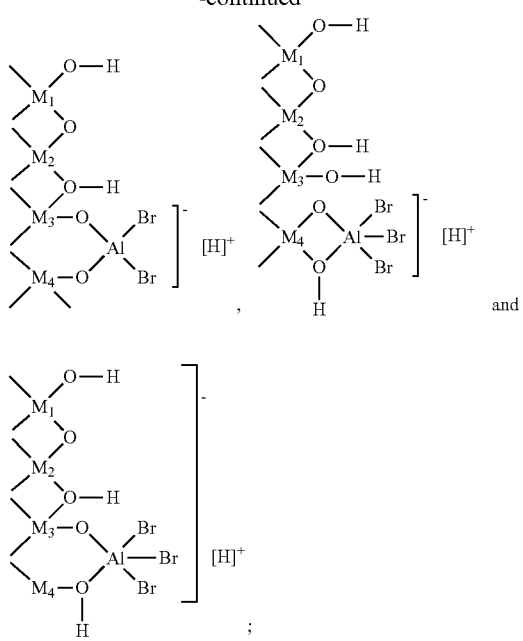

c. wherein $M_1$, $M_2$, $M_3$ and $M_4$, when present, are selected from:
      i. a first group in which $M_1$ is Al, $M_2$ is Al, $M_3$ is Al and $M_4$ is Al,
      ii. a second group in which $M_1$ is Si, $M_2$ is Si, $M_3$ is Si and $M_4$ is Si and
      iii. a third group in which $M_1$ is Si, $M_2$ is Al, $M_3$ is Si and $M_4$ is Si;
   d. wherein the metal oxide support structure is selected from an aluminum oxide based catalyst and a silicon oxide based catalyst and
   e. wherein the open-ended bonds depicted in the general formulas connect the acidic reaction site to the metal oxide support structure.

2. The composition of matter of claim 1 wherein $M_1$ is Al, $M_2$ is Al, $M_3$ is Al and $M_4$, when present, is Al.

3. The composition of matter of claim 1 wherein $M_1$ is Si, $M_2$ is Al, $M_3$ is Si and $M_4$, when present, is Si.

4. The composition of matter of claim 1 wherein $M_1$ is Si, $M_2$ is Si, $M_3$ is Si and $M_4$, when present, is Si.

* * * * *